United States Patent [19]
McGill et al.

[11] Patent Number: 5,234,673
[45] Date of Patent: Aug. 10, 1993

[54] LOW TEMPERATURE-VERY HIGH STRUCTURE SILICA AND METHODS

[75] Inventors: Patrick D. McGill, Havre de Grace; William C. Fultz, Rising Sun, both of Md.

[73] Assignee: J. M. Huber Corporation, Rumson, N.J.

[21] Appl. No.: 689,732

[22] Filed: Apr. 24, 1991

Related U.S. Application Data

[63] Continuation of Ser. No. 481,362, Feb. 20, 1990, abandoned.

[51] Int. Cl.$^5$ .................... C01B 33/12; C01B 33/18
[52] U.S. Cl. .................... 423/338; 106/287.34; 252/315.6; 423/339
[58] Field of Search .................... 423/335, 338, 339; 252/315.6; 106/287.34

[56] References Cited

U.S. PATENT DOCUMENTS

| | | | |
|---|---|---|---|
| 2,731,326 | 1/1956 | Alexander et al. | 423/338 |
| 3,967,563 | 7/1976 | Wason | 106/492 |
| 4,067,746 | 1/1978 | Wason et al. | 423/339 |
| 4,122,160 | 10/1978 | Wason | 423/339 |
| 4,155,769 | 5/1979 | Almagro | 428/402 |
| 4,243,438 | 1/1981 | Yanagida et al. | 148/11.5 |
| 4,251,281 | 2/1981 | Machurat et al. | 106/492 |
| 4,956,167 | 9/1990 | Aldcroft et al. | 423/339 |
| 4,992,251 | 2/1991 | Aldcroft et al. | 423/335 |
| 5,098,695 | 3/1992 | Newton et al. | 424/49 |

OTHER PUBLICATIONS

Wason, "Precipitated Silica", *Pigment Handbook*, vol. 1: Properties and Economics, Second Edition, John Wiley & Sons, Inc. (1988), pp. 139–159.

Wason, "Silica Gels", *Pigment Handbook*, vol. 1: Properties and Economics, Second Edition, John Wiley & Sons, Inc. (1988), pp. 175–181.

Wason, "Cosmetic Properties and Structure of Fine-Particle Synthetic Precipitated Silicas", *J. Soc. Cosmet. Chem.*, vol. 29 (Aug. 1978), pp. 497–521.

*Primary Examiner*—Olik Chaudhuri
*Assistant Examiner*—Ken Horton
*Attorney, Agent, or Firm*—Harold H. Flanders; Robert L. Price

[57] ABSTRACT

Precipitated silica gels having high surface areas and low oil absorption values are produced by a low temperature synthesis precipitation process. The precipitated silicas have unique flatting characteristics and are additionally useful as conditioning agents for food and salt and in dentifrice formulations.

5 Claims, 3 Drawing Sheets

FIGURE 3

LOW TEMPERATURE-VERY HIGH STRUCTURE SILICA AND METHODS

This application is a continuation of application Ser. No. 07/481,362, filed Feb. 20, 1990, now abandoned.

TECHNICAL FIELD

The present invention relates to novel silicic acid or silica products and, more particularly, to a method for producing synthetic precipitated silicas having new and unique properties.

BACKGROUND ART

As known in the art, commercially available silicas can broadly be divided into two basic categories. These categories are those produced from a liquid phase and those from a vapor phase process.

Vapor process silicas, called fumed and pyrogenic silicas, are prepared by reacting silicon tetrachloride vapor with an oxygen-hydrogen gas at high temperatures to produce silicon hydrogen chloride. Pyrogenic silicas have high external surface areas and differ from other silicas (e.g., gels, precipitated silicas, etc.) prepared from the liquid phase process.

Liquid phase silicas include precipitated silicas produced by acidulating an alkaline metal silicate with an acid such as sulfuric acid. Further liquid phase silicas include silica gels and colloidal silicas.

While precipitated silicas have been used in many applications, various properties thereof (such as high oil absorption values) render them unsuitable for many purposes.

In recent years, and to further expand the utility of precipitated silicas, prior art workers have developed new techniques for producing silica having new and unique properties.

Thus, there is disclosed in U.S. Pat. No. 2,731,326 a process for producing reinforced super colloidal silica aggregates consisting of extremely small, dense, amorphous silica units which are dried to produce a product which can be readily disintegrated and dispersed in a fluid or plastic medium. According to the process, aggregates of dense silica spheroidal units are reinforced by causing active silica to accrete to the aggregates. The accreted silica acts as a cement or mortar to hold spheroids together. These silica aggregates have both high surface areas and high oil absorption characteristics.

U.S. Pat. No. 3,967,563 discloses a process for precipitating a very high structure silica. In the disclosed process, the rate of acidulation is very carefully controlled, particularly at the outset of the reaction and at the point at which precipitation initially occurs. The silica product produced by this method has a very high structure, a wet cake moisture between 86–89%, an oil absorption of about 220–250 cc/100 g and a surface area of about 250–280 m$^2$/g as shown by examples 1–4.

U.S. Pat. No. 4,251,281 discloses a process for producing synthetic amorphous silica which has a surface area of between 80–310 m$^2$/g and an oil absorption index of between 240–320 cc/100 g. The process involves reacting a strong acid with an alkaline silicate solution wherein the acid is added to the solution at a variable rate to maintain a residual alkalinity of the medium substantially constant with time.

Thus, while techniques have been developed for producing amorphous precipitated silicas having various improved properties, improvements directed to such silica which have high wet cake moisture contents and reduced oil absorption values have not been made.

Inasmuch as reduced oil absorption values have the added value of lowering volatile organic compounds (VOC) requirements in coating formulations versus other precipitated silica flatting agents, there is a commercial need for silica products which have reduced oil absorption values and high wet cake moisture values. This is particularly true since present VOC regulations are in effect in certain areas of California and nationwide regulations are expected in the near future. Thus, paint and coating manufacturers are keenly interested in a low oil absorption quality for silica products that can be used as flatting pigments.

DISCLOSURE OF THE INVENTION

Accordingly, one object of the present invention is to provide a process for producing a silica product having a low oil absorption value while retaining a high wet cake moisture content. In one aspect, the present invention is directed to a low temperature approach to the synthesis of precipitated silica.

A further object of the present invention is to provide a silica product having a lowered oil absorption value and high wet cake moisture content which is useful as a flatting pigment in paints, varnishes, lacquers and similar coating compositions.

A still further object of the present invention is to provide a process for producing a silica product having a high density, a high refractive index which is similar to or more characteristic of a silica gel than typical precipitated silica products, and which is particularly resistant to milling.

A still further object of the present invention is to provide a silica product useful as a conditioning agent for foods and salt and the conditioned products.

An even further object of the present invention is to provide for a dentifrice that includes the silica product of the present invention.

In satisfaction of the foregoing objects and advantages, there is provided by the present invention a composition of matter comprising a finely-divided precipitated silica gel having an oil absorption value less than about 300 cc/100 g, a wetcake moisture value in excess of 85%, a surface area greater than about 190 m$^2$/g and a particle size distribution wherein 80% of the particles are between 3 and 7 μm.

Also provided are flatting pigments, conditioning agents, and dentifrice formulations which contain said precipitated silica gel.

The present invention also provides a method for producing the silica composition of the present invention which comprises:

a. providing an aqueous reaction medium containing an alkali metal silicate;

b. heating said aqueous reaction medium to a temperature of from about 45° C. to about 65° C.;

c. adding to said aqueous reaction medium an acidulating agent to form a slurry having a pH between about 5.0 to about 5.5;

d. collecting and washing the reaction product which comprises a silica product;

e. drying said silica product; and, optionally, f. milling said dried silica product.

The manner in which the foregoing and other objects are achieved in accordance with the present invention will be better understood in view of the following detailed description which discloses particularly advantageous method and composition embodiments for illustrative purposes.

BRIEF DESCRIPTION OF THE DRAWINGS

Aspects of the present invention will be described with reference to the annexed drawings, which are given by way of non-limiting examples only, in which.

BEST MODE FOR CARRYING OUT THE INVENTION

In producing the products of the present invention, a solution of alkali metal silicate is first charged to a reaction vessel (equipped with suitable heating and agitation equipment) with the silicate solution then being heated to a temperature in the range of from about 45° to about 65° C., preferably in the range of from about 45° to 60° C., more preferably in the range of from about 45° to 57° C., and most preferably at about 55° C. The silicate solution may, of course, be prepared in the reaction vessel itself or in situ.

As used herein, the term "alkali metal silicate" includes all the common forms of alkali silicates, as for example metal silicates, disilicates and the like. Water soluble potassium silicates and sodium silicates are particularly advantageous with the latter being preferred. The mole ratio of the alkali silicate, i.e., ratio of silicate to alkali metal has been found to contribute to some extent, depending on other reaction parameters, to the average pore size and CTAB of the silica products. Acceptable products can be made with silicate mole ratios of between 2.0 to about 3.5. Preferred silicate mole ratios, especially for sodium silicate are between about 2.3 and 2.7, and more preferably about 2.65±0.05.

After the solution has been heated to the above-noted temperature, an acidulating agent, preferably a mineral acid, is added in an amount sufficient to acidulate 100% of excess silicate, preferably 13.3% silicate, to bring the final slurry to a pH of between 5.0 and 5.5, and more preferably between 5.3 and 5.5.

The acidulating agent is added at a controlled rate. In a preferred embodiment in which a batch volume of 3,300 gallons was utilized, sulfuric acid at a concentration of about 11.4% by weight was added to 2,100 gallons of a silicate solution having a silica concentration of about 13.3% by weight at a rate of about 23.8 GPM until a pH of about 6.5 was reached. Thereafter the acid was manually added to a pH of between about 5.3 and 5.5. In this embodiment the acidulation time took about 46-48 minutes.

The acid is preferably a strong mineral acid such as sulfuric acid which is added as a dilute solution thereof with preferred results being obtained if the acidic solution comprises from about 10 to 15% by weight acid based on the total weight of the solution. In a preferred embodiment acidic solution comprises about 11.4% by weight acid, based on the total weight of the solution.

After the addition of the acidulating agent, the slurry is allowed to digest at between about 45° C. and 65° C. for between about 10 and 40 minutes, with preferred reaction conditions including a temperature of about 55° C. and a digestion period of about 20 minutes.

After the digestion step the resulting slurry is filtered, washed to reduce the $Na_2SO_4$ content, dried and milled to a sufficient particle size.

After filtering, the reaction product is washed to reduce the $Na_2SO_4$ level to less than 10% by weight, and preferably to less than 4% by weight and more preferably to 2% or less by weight. In a most preferred embodiment, the $Na_2SO_4$ level is ideally reduced to less than about 1% by weight. In this regard, it has been determined during the course of this invention, high levels of $Na_2SO_4$ affect both the oil absorption values and the surface area values, with increasing levels of $Na_2SO_4$ significantly lowering the surface area values.

Washing of the reaction product is generally conducted after filtering, however, for large batches it has been determined that diluting the reaction slurry with water before filtration will aid in reducing the $Na_2SO_4$ levels in subsequent washing procedures.

The drying of the reaction product, in addition to the reaction temperature, has been found to be a significant process variable in connection with producing the silica products of the present invention. The reaction product is dried to lower the non-structural moisture level to between about 4-6% by weight. Both oven drying and spray drying processes have been used in connection with the present invention. However, oven drying processes have been found to produce silica products having lower oil absorption values than similar products produced by spray drying processes. However, it has been found that when scaling up the process according to the present invention to utilize larger reactors, spray dying techniques should be used. Also, smaller scale processes such as those using 30 gallon reactors or less can be used in conjunction with spray dying techniques to produce products having acceptable oil absorption values.

The final product may be air milled to obtain a particle distribution wherein 80% of the particles are between 3 and 7 μm. This unique narrow particle size distribution eliminates, in many applications, the need for classifying the final product. The product, however, is generally resistant to milling.

In this specification, the wet cake moisture of the silica is an important characteristic. At a fixed set of reaction conditions, the water associated with the precipitate or the filter cake is called the structural water. The amount of water associated with one part of the dry, recoverable product is defined as the water pore volume. The amount of water associated with 100 parts of the dry recoverable product is defined as Structure Index (SI). Thus the water pore volume (PV) and SI are related to the % WCM by the following equation.

$$PV = \left( \frac{\% \ WCM}{100 - \% \ WCM} \right) \quad (1)$$

$$SI = \left( \frac{\% \ WCM}{100 - \% \ WCM} \right) \times 100 \quad (2)$$

A product with water pore volume above 6.5 or SI values above 650 is arbitrarily defined as a VHS (very high structure silica). A low structure silica (LS) is one which exhibits a water pore volume above 1.5 or SI values above 150. The log of the water pore volume or the log SI is linearly related to the % WCM.

A complete discussion of the wet cake moisture measurements and effects may be found in Journal of Society of Cosmetic Chemists, Vol. 29, p. 497-521 (August, 1978), and the disclosure therein is incorporated herein by reference. In this specification, Oil Absorption is determined by ASTM, D 281-31, and BET surface area is determined as described in J. Am. Chem. Soc., Vol. 60, p. 309-319, (1938).

Contrary to products produced by similar process of the prior art which produce amorphous precipitated silicas, the products of the invention appear to be gels. The formation of gels rather than amorphous silicas appear to result from the lowered reaction temperatures used in the process.

As discussed in detail above, the present invention is directed to a low temperature-very high structure silica product which has an oil absorption value of less than about 300 cc/100 g, a wet cake moisture in excess of 85% and a surface area greater than about 190 $m^2/g$.

As more particularly discussed in the examples which follow, the amorphous silica product of the present invention has been found to have unique properties which provide for new compositions wherein the novel very high structure lowered oil absorption silicas can be advantageously substituted for other commercially available silica products. These compositions include novel coating compositions wherein the present silica product is utilized as a flatting agent in paints, food conditioning agents, dentifrice formulations, beer chill proofing applications and edible oil absorption applications. When surface treated with a wax component, settling can be avoided and the product can be used in various coating formulations.

The method for producing the lowered oil absorption-very high structure silica gel products, as discussed above involves providing an aqueous reaction medium containing an alkali metal silicate. After heating the reaction medium to a temperature of between about 45° to about 65° C., and preferably at about 55° C., an acidulating agent is added therein to form a slurry having a pH of between about 5.0 and about 5.5, and preferably between about 5.3 and about 5.5. In particular, an acidulating agent, such as sulfuric acid, is added in a sufficient amount to acidulate 100% of excess silicate, usually about 13.3%, by weight, excess silica.

After adjusting the pH of the final slurry as discussed above, the reaction medium is allowed to digest at the temperature to which the reaction medium has been heated for a sufficient time to form the silica product which is then collected and washed prior to drying. Generally, a digestion time of about 20 minutes has been found to be sufficient for a reaction temperature of about 55° C.

The silica product is collected by a filtering process and washed to reduce the $Na_2SO_4$ level to below 10% by weight, and preferably to below 4% by weight, and more preferably to 2% or less by weight, and most preferably to less than 1% by weight.

After washing, the silica product is dried, preferably by a spray drying process to yield a product which has an oil absorption value below about 300 cc/100 g, and preferably from about 90 cc/100 g up to about 300 cc/100 g.

The following examples are presented to illustrate the invention but the invention is not considered to be limited thereto. In the examples and throughout the specification, parts are by weight unless otherwise indicated.

EXAMPLE 1

Figure 1:
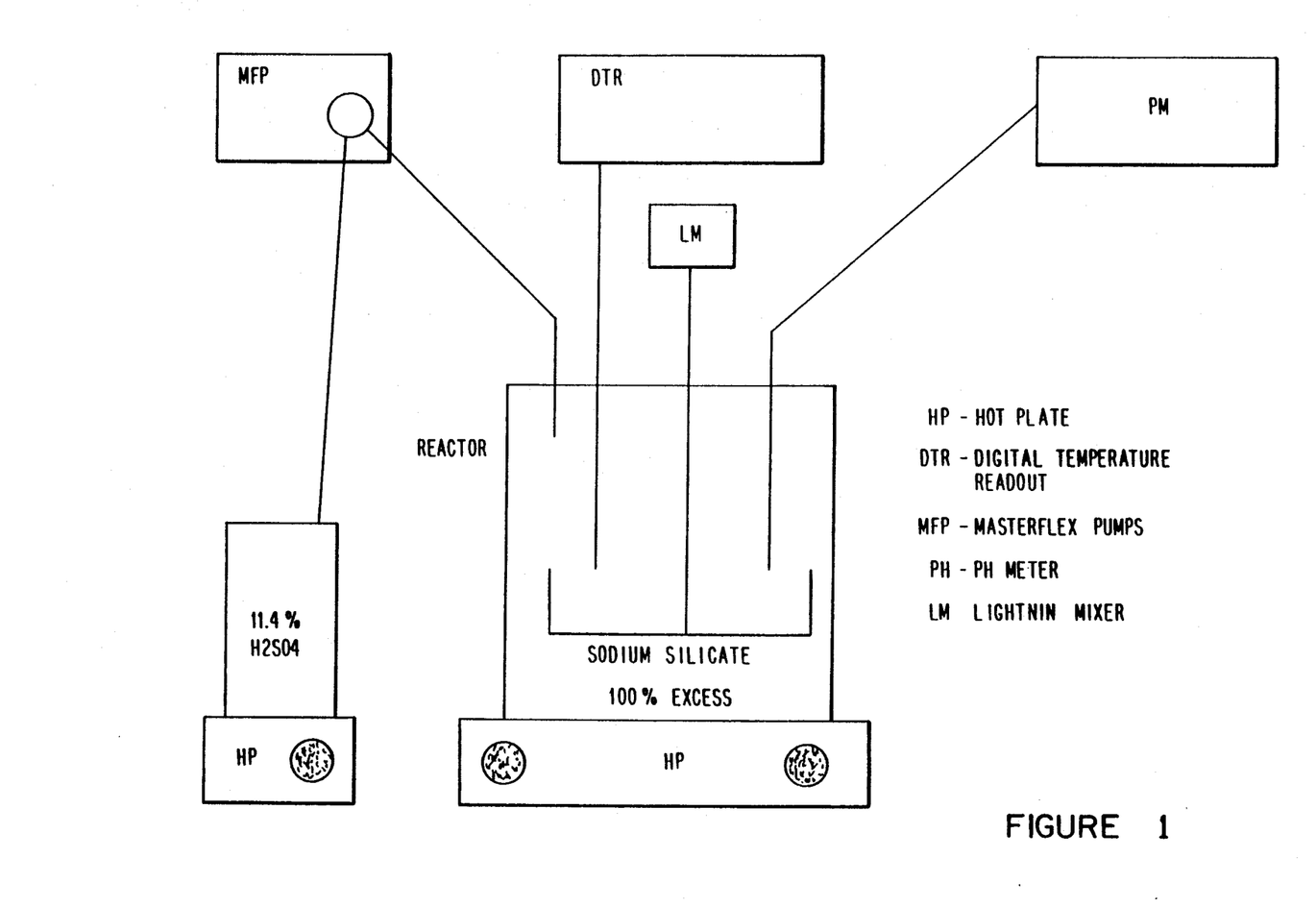
FIG. 1 is a schematic illustration of a reactor system used in conjunction with the present invention.

In this example a seven liter laboratory reactor system was used to prepare the silica. A diagram of this laboratory reactor system is displayed in FIG. 1. The batch making procedure involved an acidulation of 100% excess of (13.3%) silicate in the reactor with dilute (11.4%) sulfuric acid to final slurry pH of 5.0. A reaction temperature of 55° C. was maintained during the reaction by a hot plate in contact with the reactor. The dilute sulfuric acid was likewise heated with a hot plate. The heated sulfuric acid was pumped into the reactor by a suitable pump means as illustrated in FIG. 1. After the addition of sulfuric acid was complete, the slurry was then digested at 55° C. for 20 minutes. The reaction mixture was stirred by use of a Lightnin mixer as illustrated in FIG. 1. A temperature and pH monitor were provided as illustrated. The resulting slurry was then filtered, washed (to 2.0% or less $Na_2SO_4$ content) and oven dried to a 4-6% moisture level. The dried product was then hammermilled with a laboratory scale mill. Table I below lists the resulting product analyses, which display the following characteristics.

TABLE I

LOW TEMPERATURE - HIGH STRUCTURE SILICA SYNTHESIS IN LABORATORY REACTOR SYSTEM
Product Evaluation

| | |
|---|---|
| OIL ABSORPTION | 129 cc/100 g |
| B.E.T. SURFACE AREA | 350 $m^2/g$ |
| COULTER COUNTER APS | 29.3 $\mu m$ |
| POUR DENSITY | .313 g/ml (19.5 #/$ft^3$) |
| PACK DENSITY | .500 g/ml (31.2 #/$ft^3$) |
| Hg INTRUSION | 1.29 cc/g |
| % 325 RESIDUE | 57.8 |
| 5% pH | 7.3 |
| CTAB | 219 $m^2/g$ |
| % $H_2O$ | 9.6 |
| % LOI | 4.8 |
| % $Na_2SO_4$ | .18 |
| % $Al_2O_3$ | .13 |
| % FLUORIDE COMP | 90 |
| REFRACTIVE INDEX | 1.463 |
| % T | 88.4 |

A major point of interest from the data in Table I is the very low oil absorption value. Controlled structure technology would predict that this material should have a high oil absorption value (200-250 cc/100 g). The low oil absorption value of 129 cc/100 g obtained for this sample was due to the lower reaction and digestion temperatures used followed by oven drying of the product.

In addition to having a low oil absorption value, the silica product was also found to have a high density compared to other commercial silica products. Additionally, the silica product has a high residue value which indicates that this material is very resistant to milling. Finally, the silica product demonstrated a high refractive index, which is more characteristic of a silica gel than typical precipitated silica products.

EXAMPLE 2

In this example four batches of low temperature-high structure silica were prepared in a 30 gallon reactor. The same synthesis procedure used in the laboratory reactor of example 1 was employed in this example. The objectives for this series of batches were first to reproduce the product generated in the initial laboratory batch of low temperature high structure silica, and second to observe the effect of varying the reaction temperature in the range of 45°–70° C. Table II displays the results and evaluation of products from these four batches.

TABLE II

HAMMERMILLED SAMPLES - 30 GALLON REACTOR SERIES

| SAMPLE | A | B | C | D |
|---|---|---|---|---|
| Reaction Temp. - °C. | 45° | 55° | 55° | 70° |
| Wetcake Moisture | 87.7% | 88.4% | 86.9% | 85.2% |
| Oil Absorption (cc/100 g) | 90 | 155 | 105 | 186 |
| B.E.T. Surface Area (m²/g) | 219 | 367 | 191 | 264 |
| Pour Density (g/ml) | — | .18 | — | — |
| Pack Density (g/ml) | — | .33 | — | — |
| Hg Intrusion (cc/g) | 1.09 | 2.01 | 2.22 | 2.51 |
| % H$_2$O | 6.5 | 5.6 | 6.4 | 8.6 |
| % LOI | 4.0 | 5.3 | 4.6 | 5.5 |
| % 325 Residue | 9.63 | 8.69 | 3.88 | 3.46 |
| 5% pH | 6.9 | 6.9 | 6.8 | 6.9 |
| CTAB - (m²/g) | 166 | 232 | 157 | 183 |
| % Na$_2$SO$_4$ | 26.1 | 2.3 | 20.6 | 3.7 |
| Coulter Counter APS (m) | 15.4 | 15.4 | 12.5 | 14.3 |
| Refractive Index | 1.451 | 1.451 | 1.448 | 1.451 |
| % T | 58.1 | 81.3 | 42.0 | 91.7 |
| % Fluoride Comp. | 84 | 95 | 86 | 88 |

In reviewing the data, sample B was found to differ in character from the other 55° reaction temperature products produced in the 30 gallon reactor (sample C). In particular, lower oil absorption values and significantly lower surface area values were obtained with the latter sample. Upon closer inspection, a very high level of Na$_2$SO$_4$ (20% by weight) was also found in the latter sample. This very high Na$_2$SO$_4$ level is believed to be the cause of these changes. This high Na$_2$SO$_4$ level also indicates that washing this type of material has to be carefully controlled to obtain adequate washing.

As shown in Table II, variations in the batch reaction temperature produced a number of changes in the product character. In particular, as the reaction temperature was decreased, the oil absorption decreased and the density increased. In sample D, conducted at 70° C., the oil absorption was higher than the other samples.

Figure 2:
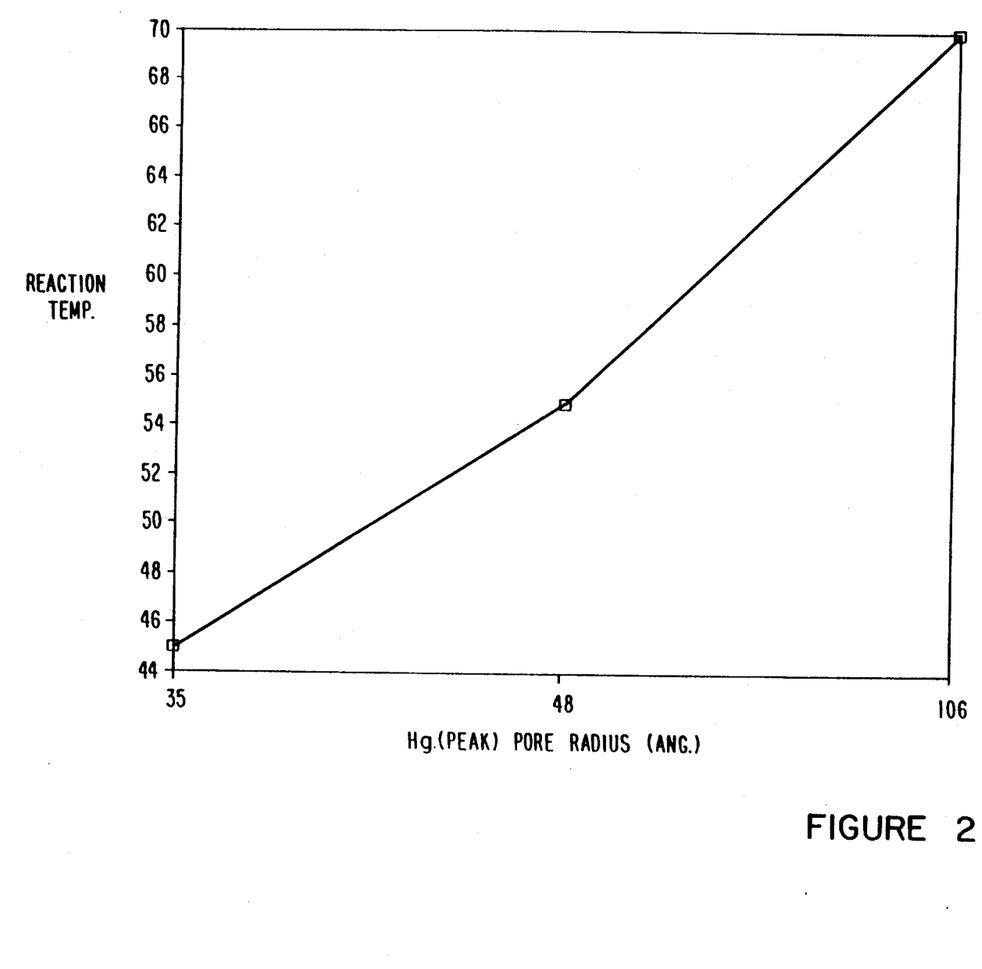
FIG. 2 is a graph illustrating the relationship between reaction temperature and Hg pore radius.

As seen from the Hg intrusion data illustrated in FIG. 2, the primary peak location (describing the pore structure) was found to shift to smaller pore radii as the reaction temperature was decreased. The Hg intrusion measurement is a way of measuring resistance to milling as an indication of change in porosity (average pore size).

Although the surface area data for the 45° C. and 55° C. batches (sample C only) has been affected by high Na$_2$SO$_4$ levels, it would be expected that surface area values would increase as the reaction temperature is decreased.

Table III lists product characteristics from samples which have been spray dried. As seen from Table III, the anhydro(lab-scale) spray dried samples were found to have significantly higher oil absorption values than those materials that were oven dried.

TABLE III

ANHYDRO SPRAY DRIED SAMPLES 30 GALLON REACTOR SERIES

| Sample | E | F | G |
|---|---|---|---|
| Reaction Temp (°C.) | 45 | 55 | 70 |
| Oil Absorption (cc/100 g) | 174/90* | 190/105* | 311/186* |
| B.E.T. Surface Area (m²/g) | 315/219* | 237/191* | 281/264* |
| Coulter Counter APS | 13.3 | 11.2 | 6.3 |

TABLE III-continued

ANHYDRO SPRAY DRIED SAMPLES 30 GALLON REACTOR SERIES

| Sample | E | F | G |
|---|---|---|---|
| % H$_2$O | 4.8 | 4.8 | 6.5 |
| % LOI | 5.4 | 4.7 | 5.8 |
| % 325 Residue | 1.12 | .13 | 6.69 |

*Oven dried data

Table IV shows product characteristics from products that have been tested for flatting properties. As seen from Table IV the 19.311 acrylic lacquer flatting data for the ACM milled samples was encouraging, when compared to a Zeothix ® 95 standard. Zeothix ® is a registered trademark of J. M. Huber Corporation for a silica flatting agent.

TABLE IV

ACM MILLED SAMPLES 30 GALLON REACTOR SERIES

| Sample | H | I | J | K | Zeothix ® 95 STD |
|---|---|---|---|---|---|
| Reaction Temperature (°C.) | 45 | 55 | 55 | 70 | |
| Oil Absorption (cc/100 g) | 120 | 165 | 130 | 200 | |
| B.E.T. Surface Area (m²/g) | 230 | — | 208 | 291 | |
| Coulter Counter APS (um) | 5.7 | 7.1 | 5.8 | 6.6 | |
| Pour Density (g/ml) | .219 | — | .207 | .106 | |
| Pack Density (g/ml) | .419 | — | .365 | .194 | |
| % H$_2$O | 2.8 | — | 3.9 | 4.7 | |
| % LOI | 4.6 | — | 4.3 | 5.8 | |
| % 325 Residue | .14 | .08 | .05 | .08 | |
| 19.311 Hegman | 4.5 | 5.5 | 6.0 | 5.25 | 6.0 |
| 60° Gloss | 9 | 6.0 | 12.5 | 5.0 | 10.0 |
| 85° Sheen | 17 | 9.0 | 22.5 | 8.0 | 31.0 |

EXAMPLE 3

In this example, the effect of the reaction temperature was investigated by producing three low temperature, high structure silica batches in a 400 gallon reactor system. The reaction temperatures of the three batches were 45° C., 55° C. and 70° C. The reactor conditions and properties of the products produced after various reaction temperatures are given in Table V below.

TABLE V

Reaction Temperature Change vs. Product Properties and Process Variables

| | 70° C. | 55° C. | 45° C. |
|---|---|---|---|
| Reaction Temperature (°C.) | | | |
| Silicate in Reactor (l) | 582 | 582 | 582 |
| H$_2$SO$_4$ pump rate (l/min.) | 6.6 | 6.7 | 6.7 |
| Final pH | 4.8 | 5.0 | 5.0 |
| Opalescence point (min.) | 24.4 | 24.3 | 24.6 |
| Volume of H$_2$SO$_4$ added (l) | 298 | 319 | 294 |
| Addition time (min.) | 51.1 | 47.5 | 44.92 |
| Wet cake moisture | 86.6 | 88.7 | 88.9 |
| Oil Absorption cc/100 g | 241 | 249 | 239 |
| BET Surface area (m²/g) | 284 | 382 | 450 |
| APS (Mm) | 2.1 | 3.7 | 4.4 |
| Pour Density (#/ft³) | 2.8 | 5.7 | 10.4 |
| Pack Density (#/ft³) | 4.8 | 9.8 | 15.8 |

TABLE V-continued

Reaction Temperature Change vs. Product Properties and Process Variables

| | | | |
|---|---|---|---|
| Hg Intrusion/peak location | 4.47/100A | 3.76/35A | 2.51/23A |
| % H$_2$O | 2.9 | 4.1 | 6.8 |
| % LOI | 4.2 | 4.6 | 4.9 |
| % 325 Residue | .06 | L.01 | L.1 |
| 5% pH | 7.7 | 8.2 | 8.0 |
| CTAB (m$^2$/g) | 189 | 326 | 318 |
| Air mill Air temp (°F.) | 250 | 250 | 250 |
| Feed Rate (#/hr) | 2.66 | 1.6 | 1.6 |
| Wall Pressure (Psi) | 35 | 65 | 65 |
| Feed Pressure (Psi) | 100 | 100 | 100 |
| 19.311 Hegman | 6 | 6 | 4.5 |
| 60° Gloss | 4 | 4 | 6 |
| 85° Sheen | 23 | 17 | 14 |
| Other Flatting Data Hegman/Gloss/Sheen | 6.5/6.5/41 5.5/7/49 5.0/5/28 | 5.5/4/14 5.25/4/11 | 4.5/5.5/15 |

The data from this example indicates that a reaction temperature of about 55° C. produces a product having an optimum oil absorption value.

EXAMPLE 4

In this example eight low temperature—high structure batches were prepared in a 400 gallon reactor system. Several production concerns were addressed in this series where a 55° C. reaction temperature was primarily used.

Washing the product to a desirable Na$_2$SO$_4$ level (2-4%) was a primary goal in this example. The standard production technique of using a rotary filter to filter and wash the wet cake produced a product having an unacceptable Na$_2$SO$_4$ level (in excess of 10% Na$_2$SO$_4$). A 24" plate and frame filter was also found to produce unacceptable product. The most appropriate technique was found to be a dilution of the reactor slurry with water (1.5×batch volume) before filtration on the rotary filter. This technique resulted in a 2-4% Na$_2$SO$_4$ level in the dry product. It was found that 24-32 pounds of wash water per pound of dry product was required by this washing technique.

A major processing difference, when changing from the 30 gallon reactor of example 2 to the 400 gallon reactor of this example, is that oven drying was used in the 30 gallon system as compared to spray drying in the 400 gallon system. The change in drying technique from oven to spray drying dramatically increased the oil absorption of the product. This effect was seen also when samples of wet cake from 30 gallon reactor batches were spray dried in the lab-scale anhydro spray dryer. A comparison of spray dried and oven dried samples from a 400 gallon reactor batch is displayed in Table VI.

The surface area values (B.E.T. and CTAB) appear to increase for spray dried samples as compared to the oven dried samples.

TABLE VI

BATCH 6, 7, 8 PRODUCT COMPARISON

| | O S.D. ACM MILLED PRODUCT 6 | P S.D. ACM MILLED PRODUCT 7 | Q S.D. ACM MILLED PRODUCT 8 |
|---|---|---|---|
| Oil Absorption (cc/100 g) | 278 | 233 | 256 |
| B.E.T. Surface Area (m$^2$/g) | 355 | 370 | 371 |
| APS (um) | 7.9 | 9.8 | 8.3 |
| Pour Density (g/ml) | .102 | .096 | .102 |
| Pack Density (g/ml) | .156 | .167 | .172 |
| Hg Intrusion (cc/g) | — | 3.55 | 3.92 |
| % H$_2$O | 5.7 | 5.6 | 4.8 |
| % LOI | 5.1 | 5.4 | 5.0 |
| % 325 Residue | .01 | .01 | .02 |
| 5% pH | 7.7 | 7.6 | 7.9 |
| CTAB - (m$^2$/g) | — | 281 | 283 |
| % Na$_2$SO$_4$ | 2.2 | 3.2 | 2.6 |

In addition, a decrease in the product pour and pack densities was also observed for milled, spray dried product as compared to the milled oven dried sample.

Table VII displays product analyses of batches 6, 7, and 8 prepared after a satisfactory washing technique was developed. The data from this comparison indicates that consistency in product quality was maintained for these three batches.

The product analysis in Table VII is with respect to flatting characteristics in different types of clear coatings and a comparison with commercial products.

Zeothix ®95 is a silica flatting pigment sold by J. M. Huber Corporation. Syloid ®74, Syloid ®234, and Syloid ®235 are commercial flatting pigments sold by W. R. Grace. Lo-vel ®28 is a flatting pigment sold by PPG Industries, Inc.

TABLE VII

New Flatting Silica ACM-1 Milled Product

| Product | Hegman | Gloss | Sheen | |
|---|---|---|---|---|
| Acrylic Lacquer Test (19.311) | | | | Settling |
| Zeothix ® 95 | 6.0 | 10.0 | 31.0 | 10 |
| Sample | 5.0 | 2.5 | 4.5 | 5 Soft |
| Trade Sales Varnish (19.608) | | | | |
| Syloid ® 74 | 6.0 | 9.0 | 12.0 | |
| Zeothix ® 95 | 5.75 | 12.0 | 27.0 | |
| Sample | 5.25 | 4.0 | 4.0 | |
| Coil Coating (19.609) | | | | Viscosity |
| Syloid ® 74 | 5.5 | 26 | 66 | 710/615 |
| Zeothix ® 95 | 5.5 | 34 | 76 | 4800/1500 |
| Lo-Vel ® 28 | 5.25 | 19 | 41 | 4120/1450 |
| Sample | 5.0 | 10 | 2 | 2360/1875 |
| Nitrocellulose Lacquer (19.308) | | | | |
| Zeothix ® 95 | 6.0 | 8.0 | 21.0 | 530 |
| Syloid ® 74 | 6.0 | 6.5 | 8.5 | 180 |
| Syloid ® 234 | 7.0 | 6.0 | 28.0 | 210 |
| Syloid ® 235 | 6.5 | 4.5 | 9.5 | 180 |
| Sample | 5.25 | 3.5 | 3.5 | 210 |

EXAMPLE 5

In this example several milling techniques were investigated for the 400 gallon reactor products. Hammer-milling, as in the 30 gallon reactor system, produced materials with poor flatting performance (too much 325 residue).

Despite the significant increase in the oil absorption value, good flatting results were obtained for these products using an ACM mill. Table VIII displays the results of a flatting evaluation of sample "O" in various coating systems. (The other products were found to perform in a similar manner). Slightly lower Hegman values were obtained as compared to Zeothix ®95 and some of the competitive products.

TABLE VIII

| SAMPLE | | OIL ABSORPTION (cc/100 g) |
|---|---|---|
| R | 30 Gallon Reactor - 55° C. Rx temp. - oven dried | 130 |
|   | 30 Gallon Reactor - 55° C. Rx temp. - spray dried (Anhydro) | 190 |
| S | 30 Gallon Reactor - 45° C. RX temp. - oven dried | 120 |
|   | 30 Gallon Reactor - 45° C. RX temp. - spray dried (Anhydro) | 174 |
| T | 30 Gallon Reactor - 70° C. Rx temp. - oven dried | 200 |
|   | 30 Gallon Reactor - 70° C. Rx temp. - spray dried (Anhydro) | 311 |
| U | 400 Gallon Reactor - 55° C. Rx temp. - oven dried | 169 |
|   | 400 Gallon Reactor - 55° C. Rx temp. - spray dried (Pilot Plant) | 233 |
| V | 400 Gallon Reactor - 55° C. Rx temp. - oven dried | 186 |
|   | 400 Gallon Reactor - 55° C. Rx temp. - spray dried (Pilot Plant) | 231 |

A 4" air mill was evaluated to determine its ability to produce desirable flatting properties in the product. Milling trials were conducted to determine the optimized milling parameters to produce a product having the best flatting properties. The optimum milling conditions for batch 6 product were:

Feed rate = 2.5 lb/hr
Wall pressure = 65 psi
Feed pressure = 104 psi
Mill air temperature = 250° F.

These conditions produced material with the following 19.311 acrylic lacquer results:

Hegman = 5.25
60° F. Gloss = 4.5
85° F. Sheen = 16.5
10 RPM Viscosity = 310 CPS
100 RPM Viscosity = 311 CPS In the following examples the silica products were evaluated in various application areas other than flatting.

EXAMPLE 6

In this example the process of the present invention was scaled up to produce a batch size of approximately 2000 pounds. Three batches of the product of the present invention were produced utilizing the reaction parameters in Table IX below.

TABLE IX

| REACTION PARAMETERS | |
|---|---|
| Batch Size: | 2,000 lb |
| Batch Volume | 3,300 gallons |
| Total Volume of F.W. Silicate | 2,100 gallons |
| Silicate Mole Ratio | 2.65 + or −0.05 |
| Silicate Concentration | 13.3% + or −0.2% |
| Sulfuric Acid Concentration | 11.4% + or −0.2% |
| Sulfuric Acid Rate | 23.8 + or −0.5 GPM |
| Sulfuric Acid Temperature | 92° F. + or −2° F. |
| Silicate Temperature | 131° F. (Max) |
| Reaction Temperature | 131° F. + or −2° F. |
| Digestion Temperature | 131° F. + or −2° F. |
| Digestion Time | 20 minutes |
| Final Slurry pH | 5.3–5.5 |
| Acid Time to pH 5.3–5.5 | 46–48 minutes |

In each of these three batches, 2,100 gallons of fresh water silicate were added to the reactor prior to heating to 131° F. The acid was added at a rate of approximately 23.8 GPM to obtain a pH of about 6.5. After reaching a pH of 6.5, the acid was added manually to a pH between 5.3 and 5.5 using an acid adjustment valve. The approximate acid addition time was 46–48 minutes. The digestion time was approximately 20 minutes at 131° F. during which time the pH was maintained between 5.3 and 5.5.

The following general filtration parameters were utilized for recovering products in the batches:

| Optimum Drum Speed | 7 minutes. per revolution |
|---|---|
| Vacuum Range | 12–15 inches of water |
| Wash Water Rate Range | 20 to 25 GPM |
| Water Added to Filter Screw | 1.5–2.0 GPM |
| Sulfate Obtained | 1.4–3.0% |

The filter time for the batches was from 4.5 to 5 hours resulting in a filter rate of approximately 440 pounds per hour. The following Table X shows the amount of sulfate liquor generated.

TABLE X

| BATCH NO. | LIQUOR PRODUCED (GAL) | GALLONS OF LIQUOR/ LB OF PRODUCT |
|---|---|---|
| 1 | 11,763 | 5.9* |
| 2 | 14,800 | 7.4* |
| 3 | 12,556 | 6.2* |

*Based on theoretical yield

Upon drying, batch 1 yielded 1,800 pounds of dry product, batch 2 yielded 1,700 pounds of dry product, and batch 3 yielded 1,850 pounds of dry product. The expected yield was 2,000 pounds. The differences between theoretical and expected yield can be attributed to samplings, spills and clean up between batches. Utilizing specific gravity results with the percent solids, the reactor was generating approximately 3.6 million BTUs per hour under maximum production conditions. Approximately 300 pounds per hour of dried product were produced and 3,450 pounds of water were dried each hour. The maximum theoretical drying capacity was 3,850 pounds of $H_2O$ per hour.

EXAMPLE 7

In this example a 2,000 pound batch size of product was produced and tested as a suitable flatting agent for lacquer systems. In this example, the reaction process of the previous example was modified so that 2.65 molar ratio silicate could be replaced by 3.3 molar ratio silicate according to the following equation:

$5Na_2O.2.65SiO_2 + H_2SO_4$ $4Na_2.O.3.31SiO_2 + Na_2SO_4 + H_2O$

The raw materials utilized in modifying the previous example to utilize a different molar ratio silicate were as follows in Table XI.

TABLE XI

| RAW MATERIALS | | | |
|---|---|---|---|
| | Silicate | $H_2SO_4$ | Sulfate Water |
| MR | 3.32 | — | — |
| concentration g/l | 274.3 | 11.22 | 41.4 |
| temperature °C. | 55 | 50 | 55 |
| solids content % | 22.63 | — | — |
| specific gravity | 1.212 | — | 1.030 |
| $SiO_2$ | 17.26 | — | — |

The reaction was fed sulfate water, fresh water and excess silicate. The reaction medium was heated to 55° C. Sulfuric acid was added until the final pH was reached (about 50 minutes). The final pH was maintained during 20 minutes digestion. While adding sulfuric acid, the opalescence points were obtained between 18.5–21 minutes from the beginning of precipitation. The reaction parameters are summarized in Table XII below.

During this example, three batches were made. The analysis results of the reactor samples are displayed in Table XIII.

TABLE XII

| REACTION PARAMETERS | | |
|---|---|---|
| Batch Volume | 1 | ≈12500 liters |
| Reaction Medium: | | |
| Excess silicate | 1 | 4500 |
| Sulfate water | 1 | 3280 |
| Fresh water | 1 | 970 |
| Precipitation temperature | °C. | 55 |
| Precipitation time | min. | ≈50 |
| $H_2SO_4$ rate | l/min. | 90 |
| Final pH | | 5.3–5.5 |
| Digestion time | min | 20 |
| Digestion temperature | °C. | 55 |

TABLE XIII

| Batch | Concentration of Pigment | pH | Oil Absorption |
|---|---|---|---|
| 1 | 80.0 g/l | — | — |
| 2 | 81.6 g/l | 3.37 | 155 cc/100 g |
| 3 | 85.2 g/l | 5.94 | 156 cc/100 g |

Reactor slurries were diluted in ratio 1:1 with water before filtration. By this technique it was possible to decrease sulfate content of slurries to the desired level as set forth in Table XIV below. Dry matter capacity of filtration was about 300 kg/h.

TABLE XIV

| Batch | Solids % | pH | $Na_2SO_4$ % | Oil Abs cc/100 g | CTAB $m^2/g$ |
|---|---|---|---|---|---|
| 1 | 18.5 | 8.8 | 0.00 | 211 | 177 |
| 2 | 9.6 | 7.9 | 0.16 | 198 | 183 |
| 3 | 11.2 | 7.6 | 0.49 | 195 | 214 |

Dry matter capacity of spray drying was about 350 kg/h. Table XV displays the test results of the spray dried basestock.

TABLE XV

| SPRAY DRIED BASESTOCK | | | | |
|---|---|---|---|---|
| | | Target Value | Basestock X | Δ |
| Moisture | % | 3–6 | 5.3 | 0.3 |
| pH 5% | | 7–8 | 8.1 | 0.0 |
| $Na_2SO_4$ | % | <1.5 | 0.24 | 0.05 |
| Oil absorption | cc/100 g | 250–300 | 266 | 4.0 |
| CTAB | $m^2/g$ | >250 | 261 | 18.5 |
| APS | μm | — | 41.8 | 2.7 |

EXAMPLE 8

In this example a Verti-Press (available from Filtra-Systems Company, Filtra Systems Technology, Farmington, Mich.) was evaluated for its ability to filter the low temperature, high structure silica. In this example filtration variables were investigated to optimize filtration and washing of this material.

The silica gel product was dewatered and washed in a fully automatic Verti-Press Filter with 10 square feet of filter area. All Filter runs were made in one day from a single batch of product. The batch temperature for Run #1 was 120° F. and dropped steadily to 105° F. for Run #15. The first four runs established the filter's feed rate, throughput capacity and cake dryness. Filter Runs #5 through #10 varied the cake wash water volume and Runs #11 through #15 optimized the cake wash efficiency.

The properties of the samples before and after filtering are given in Table XVI below.

TABLE XVI

| Washing Sample | Trial | % $Na_2SO_4$ | Weight (Kg) | Wetcake % Solids | Dry Product Weight (Kg) | Dry Product % $Na_2SO_4$ | Kg Wash Water/ Kg Product | Pressure (PSI) |
|---|---|---|---|---|---|---|---|---|
| 1 | 1 | 0.7 | 7.5 | 18.8 | 1.57 | 3.3 | 21.7 | 100 |
| 2 | 2 | 1.7 | 12.6 | 20.4 | 2.86 | 7.5 | 6.0 | 100 |
| 3 | 3 | 2.8 | 8.7 | 22.4 | 2.17 | 11.2 | 7.7 | 100 |
| 4 | 4 | 2.8 | 10.2 | 19.0 | 2.15 | 13.3 | 10.2 | 100 |
| 5 | 5 | 2.0 | 9.7 | 20.6 | 2.22 | 8.7 | 12.1 | 100 |
| 6 | 6 | 1.5 | 9.7 | 19.0 | 2.05 | 7.1 | 14.9 | 100 |
| 7 | 7 | 1.1 | 8.8 | 18.4 | 1.80 | 5.4 | 22.3 | 100 |
| 8 | 8 | 1.3 | 9.0 | 19.8 | 1.98 | 5.9 | 23.1 | 100 |
| 9 | 9 | 1.5 | 8.3 | 19.0 | 1.75 | 7.1 | 30.0 | 100 |
| 10 | 10 | 0.05 | 6.9 | 21.6 | 1.64 | 0.2 | 32.3 | 100 |
| 11 | 11 | 2.8 | 9.1 | 20.6 | 2.07 | 12.24 | 12.8 | 100 |
| 12 | 12 | 3.3 | 9.7 | 20.4 | 2.20 | 14.6 | 12.0 | 90 |
| 13 | 13 | 0.8 | 9.9 | 20.6 | 2.25 | 3.5 | 11.8 | 80 |
| 14 | 14 | 0.7 | 10.9 | 19.4 | 2.35 | 3.2 | 25.7 | 75 |
| 15 | 15 | 0.2 | 9.5 | 21.8 | 2.30 | 0.8 | 15.8 | 60 |

The filter was fed slurry from a batch tank using an air driven diaphragm pump. After the filter chamber was filled with a set volume of slurry, the filter header was flushed with clean water. Compressed air was introduced into the chamber above the slurry at 100 PSI. The diaphragm was then unfolded and squeezed the cake at 100 PSI. The diaphragm was retracted and wash water was pumped into the filter on top of the cake. The diaphragm then squeezed the wash water through the cake at 100 PSI. The diaphragm was then retracted for a second time and the cake was discharged. The total cake was weighed and samples were taken to determine cake percent solids and conductivity. The parameters of the filtering procedure are set forth on Table XVII below.

duce the driest possible cake. This procedure resulted in a more efficient wash.

The Verti-Press is a versatile dewatering filter which adapts easily to a wide range of products. The filter has more than twelve adjustable parameters which allow the unit to optimize the final properties of each cake. They involve belt selection, belt coating, squeeze pressure, squeeze time, air fill time, air blow time, etc., yet the Verti-Press is the simplest filter of its type with only three moving parts, the end seals, diaphragm and conveyor belt.

TABLE XVII

| RUN # | CYCLE TIME MIN. | SQUEEZE/AIR BLOW TIME | CAKE WT./SQ.FT. | CAKE % SOLIDS | WASH WATER/# OF PRODUCT | WASH WATER TEMP. | CAKE CONDUCTIVITY | CAPACITY #/HR./SQ.FT. |
|---|---|---|---|---|---|---|---|---|
| 1 | 20.72 | 60 SEC/30 SEC | .75 KG | 18.8 | 2.9 GAL/LB. | 128 F. | 3300 | 0.89 |
| 2 | 28.2 | 90/15 | 1.26 | 20.4 | 0.8 | 128 | 7700 | 1.18 |
| 3 | 15.67 | 120/15 | .87 | 22.4 | 1.0 | 130 | 8500 | 1.64 |
| 4 | 12.05 | 120/15 | 1.02 | 19.0 | 1.4 | 130 | 7780 | 2.12 |
| 5 | 17.1 | 120/15 | .97 | 20.6 | 1.6 | 130 | 3200 | 1.54 |
| 6 | 15.82 | 120/15 | .97 | 19.0 | 2.0 | 130 | 6700 | 1.53 |
| 7 | 21.83 | 120/20 | .88 | 18.4 | 3.0 | 120 | 4900 | 0.97 |
| 8 | 21 | 120/20 | .90 | 19.8 | 3.0 | 145 | 6550 | 1.12 |
| 9 | 22.17 | 120/20 | .83 | 19.0 | 4.0 | 155 | 3860 | 0.93 |
| 10 | 26 | 120/15 | .685 | 21.6 | 4.3 | 150 | 400 | 0.75 |
| 11 | 15.33 | 120/15 | .905 | 20.6 | 1.7 | 150 | 6300 | 1.60 |
| 12 | 18 | 120/15 | .97 | 20.4 | 1.6 | 150 | 8500 | 1.45 |
| 13 | 19.92 | 180/15 | .985 | 20.6 | 1.6 | 150 | 4380 | 1.34 |
| 14 | 27.6 | 180/15 | 1.09 | 19.4 | 3.4 | 150 | 1150 | 1.01 |
| 15 | 25.72 | 240/15 | .95 | 21.8 | 2.1 | 145 | 2100 | 1.06 |

The filter cakes were ⅜" thick containing 19 to 22% solids. The cakes were somewhat inconsistent in thickness due to the "gelatinous" nature of the solids. The forming cakes moved around or flowed inside the filter as the diaphragm squeezed the material at 100 PSI. For materials like silica gel it appeared that a stiffener should be added to the rubber diaphragm to produce an even cake.

Some wetness was observed on the edge of the filter cakes on Runs #1 through #9. It was believed this wetness was residual wash water left on the coated edge of the belt. This liquid would normally be driven through the cake and belt during the cake air blow. The silica gel cakes, however, cracked resulting in the air short circuiting through the cracks. The inefficient air blow left the edge of the cakes wet. It appeared that some of this wetness was slurry which had not been efficiently squeezed at 100 PSI. When the unstiffened diaphragm squeezed the cake, the rubber wrinkled and folded and was unable to reach into the corners to squeeze the outside edge of the cake efficiently. A diaphragm stiffener would have reduced the cake wetness. A new filter belt was installed after Run #9. The new belt was made of the same polyester material as the first belt, but contained no top edge coating. The new belt eliminated the cake wetness.

Figure 3:
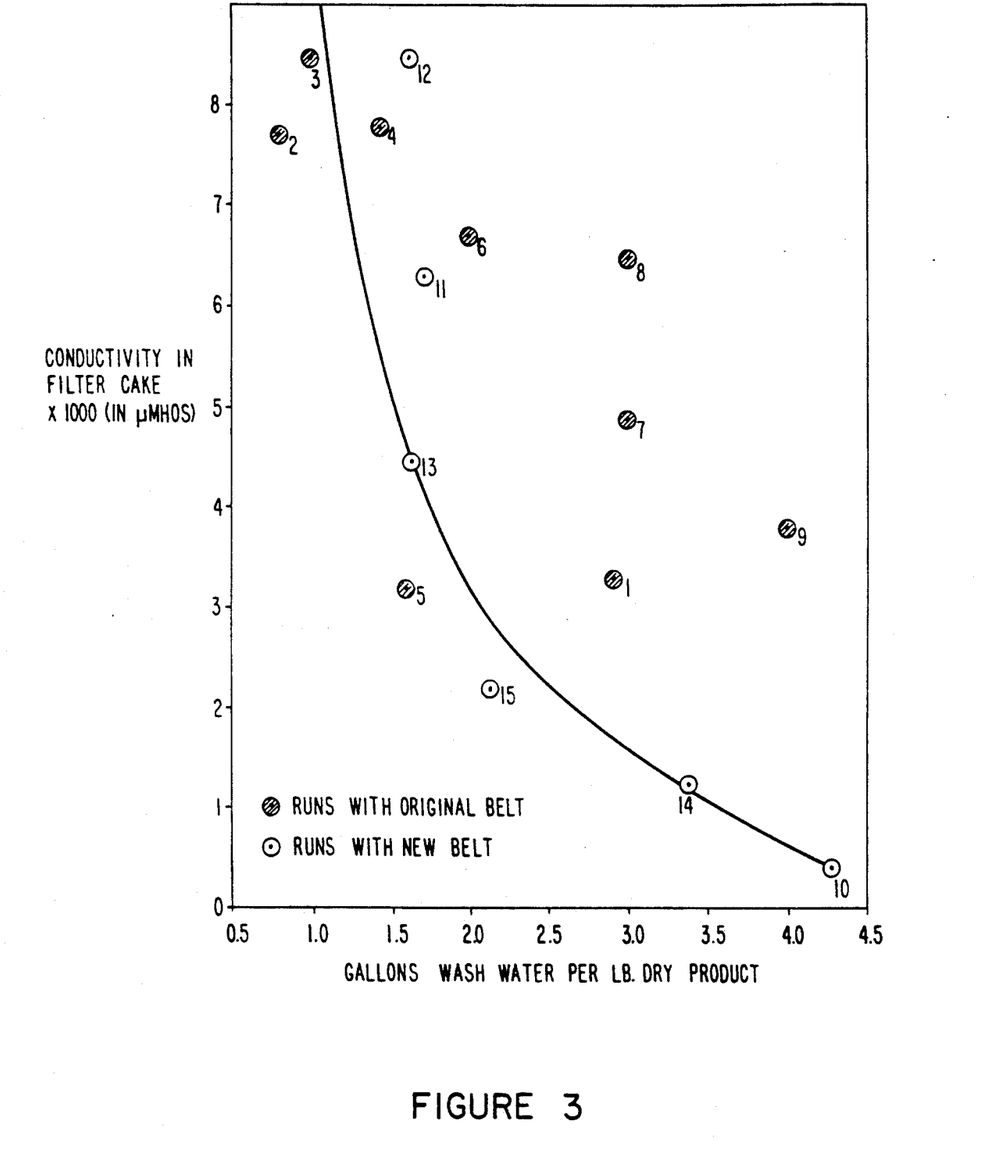
FIG. 3 is a graph illustrating the relationship between cake conductivity and wash water volume for a filtering process, utilized in one embodiment of the present invention.

FIG. 3 shows a plot of cake conductivity versus wash water volume. As seen from FIG. 3, the cake washing was very inconsistent prior to installation of the new filter belt. The silica gel was difficult to wash even with the new belt. This was because the gel formed a very tight cake which easily cracked. Once the cake cracked, the wash water "channeled" through the cracks instead of flowing uniformly through the cake. The tight cake resulted in an inefficient wash. To control the physical properties of the cakes, the first diaphragm squeeze cycle was modified. The pressure of the squeeze was lowered to 75 and 65 PSI for Runs #14 and #15 respectively. The second squeeze was set at 100 PSI to pro- Based on the results of this experiment, it is noted that the percent solids of the wet cake samples were increased from about 12% to as high as 22%. Moreover, it appears that the unit weight of the wash water to product has been reduced from the 16-20 value (for the rotary filter) to as low as 12 for a similar percent $Na_2SO_4$ level on the conveyor press. Finally, it appears that optimized dewatering and washing conditions may be obtained at lower filtration pressures. In this regard, it was noted that the cake is compacted to a lesser degree and the wash water is more easily pushed through the cake.

EXAMPLE 9

In this example, properties of silica products which were dried utilizing a Verti-Press were evaluated to determine their characteristic properties. The properties of these products are listed in Table XVIII below.

TABLE XVIII

|  | Sample 1 | Sample 2 |
|---|---|---|
| % LOI | 4.9 | 5.1 |
| % $H_2O$ | 4.6 | 4.1 |
| % Solids |  |  |
| 325 Mesh Residue (% Retained) | .29 | .30 |
| pH (5%) | 7.2 | 7.1 |
| Oil Absorption (cc/100 g) | 162 | 160 |
| Surface Area (m²/g) | 307 | 336 |
| Coulter APS (μm) | 7.5 | 8.1 |
| Valley Abrasion (mg loss) | 5.3 | 4.1 |
| CTAB S/A Anhydrous | 238 | 249 |
| Pour Density #/cu. ft. | 10.23 | 9.91 |
| Pack Density #/cu. ft. | 17.83 | 16.87 |
| Low Pressure | .4297 | .3621 |
| High Pressure | 1.7819 | 1.7734 |
| Totals | 2.21 | 2.14 |

These products were incorporated as a filler in an acrylic lacquer resulting in the properties set forth in Table XIX below.

TABLE XIX

|  | Sample 1 | Sample 2 |
|---|---|---|
| Product | Silica | Silica |
| Hegman | 5.5 T | 5.5 T |
| 60° gloss | 6.5 | 6.0 |
| 85° sheen | 10.0 | 8.5 |
| Settling (one week @ 50° C.) | 0 | 0 |
| Brookfield Viscosity |  |  |
| — 10 RPM | 290 | 310 |
| —100 RPM | 312 | 319 |
| Temp, °F. | 70 | 70 |
| T.I. | .93 | .97 |

EXAMPLE 10

In this example the silica products of the present invention were evaluated in salt conditioning tests (Table XX). Various types of silica products of the present invention and salt conditioning standards were used in this series of tests with Cargill and Diamond crystal fine flour salt. The spray dried, hammermilled silica product of the present invention performed the best, exceeding the performance of Zeolex ® 23A, but was not as good as TCP for the same loading. Zeolex ® is a trademark of J. M. Huber Corporation for a commercial silicate conditioning agent.

TABLE XX

LOW TEMPERATURE-VERY HIGH STRUCTURE SILICA AS A SALT CONDITIONER

| DESCRIPTION | LOADING | DIAMOND CRYSTAL-FINE FOUR SALT (% CAKING) | CARGILL SALT (% CAKING) |
|---|---|---|---|
| SD-HAMMERMILLED PRODUCT | 1.0 | 50.3 | 5.1 |
|  | 1.6 | 54.9 | 5.2 |
| SD-ACM MILLED PRODUCT | 1.0 | 68.4 | 7.7 |
|  | 1.6 | 66.1 | 10.2 |
| OVEN DRIED-ACM MILLED PRODUCT | 1.0 | 63.5 | 6.0 |
|  | 1.6 | 62.9 | 10.5 |
| ZEOLEX 23A | 1.0 | 67.3 | 10.9 |
|  | 1.6 | 70.3 | 14.9 |
| TCP* | 1.0 | 32.0 | 3.4 |
|  | 1.6 | 46.1 | 0.9 |
| CONTROL (UNTREATED) | — | 94.6 | 8.3 |

*TCP tri-calcium phosphate

EXAMPLE 11

In this example the silica product of the present invention was tested for use as a dentifrice abrasive. Table XXI lists the formulations of the dentifrice samples and XXII displays the results of performance of the present product in dentifrice testing. This data indicates the refractive index value is one characteristic (dentifrice related) of the present material which is of interest. The refractive indices for the present invention are greater than those obtained from more typical precipitated silicas. This quality tends to give better optical properties in gel toothpaste formulations.

TABLE XXI

DENTIFRICE POPULATIONS

|  | Formulation A | Formulation |
|---|---|---|
| Glycerine 99.5% | 160.00 g | 156.50 g |
| CMC - 7MF | 5.00 g | 5.50 g |
| Sorbital 70% Solution | 475.48 g | 679.57 g |
| Deionized H$_2$O | 84.09 g | 0.00 g |
| Sodium Fluoride | 2.43 g | 2.43 g |
| Disodium Phosphate | 10.00 g | 8.00 g |
| Monosodium Phosphate | 2.00 g | 2.00 g |
| Sodium Saccharin | 3.00 g | 3.00 g |
| Carbowax 600 | 30.00 g | 30.00 g |
| Abrasive Silica | 200.00 g | 100.00 g |
| Color Blue #1 0.1% Sol. | 3.00 g | 3.00 g |
| S.L.S. | 15.00 g | 5.00 g |
| Flavor | 10.00 g | 5.00 g |
|  | 1000.00 g | 1000.00 g |

TABLE XXII

DENTIFRICE TESTING

|  | Formulation A (30 Gallon Reactor) | Formulation B (400 Gallon Reactor) |
|---|---|---|
| % Fluoride Compatibility | 95 | 96 |
| % T | 81.3 | 97.1 |
| Refractive Index | 1.451 | 1.457 |
| RDA | 12 | 5 |
|  | (20% Gel loading) | (10% Gel loading) |
| Valley Abrasion (mg loss) | 5 | 2 |
| Viscosity (CPS)-(Helipath) 24 hr | | 175,000 |
| 1 wk | | 216,600 |
| 3 wk | | 241,700 |
| 6 wk | | 260,000 |

Although the invention has been described with reference to particular means, materials and embodiments, from the foregoing description, one skilled in the art can easily ascertain the essential characteristics of the present invention and various changes and modifications may be made to adapt the various usages and conditions without departing from the spirit and scope of the present invention as described in the claims that follow.

We claim:

1. A composition of matter comprising a finely-divided precipitated silica gel having an oil absorption value less than about 200 cc/100 g, a wet cake moisture value in excess of 85%, a surface area greater than about 190 m$^2$/g and a particle size distribution wherein 80% of the particles are between 3 and 7 μm, said silica gel being formed at a reaction temperature of from about 45° C. to about 65° C.

2. A composition according to claim 1 which has a sulfate content of less than 2.0 wt. %.

3. A composition according to claim 1 which has a sulfate content of less than 1.0 wt. %.

4. A coating composition containing a flatting pigment which comprises the silica of claim 1.

5. A composition of matter comprising a finely-divided precipitated silica gel having an oil absorption value less than about 200 cc/100 g, a wet cake moisture value in excess of 85%, a surface area greater than about 190 m$^2$/g and a particle size distribution wherein 80% of the particles are between 3 and 7 μm, said silica gel produced by providing an aqueous reaction medium containing (a) an alkali metal silicate; (b) heating said aqueous reaction medium to a temperature of from about 45° C. to about 65° C.; (c) adding to said aqueous reaction medium an acidulating agent to form a slurry having a pH between about 5.0 to about 5.5; (d) collecting and washing the reaction produce which comprises a silica product; (e) drying said silica product; and (f) milling said dried silica product.

* * * * *